US012329385B2

(12) United States Patent
Hughett, Sr. et al.

(10) Patent No.: US 12,329,385 B2
(45) Date of Patent: Jun. 17, 2025

(54) APPARATUS AND METHODS FOR OCCLUDING AN ANATOMICAL STRUCTURE

(71) Applicant: AtriCure, Inc., Mason, OH (US)

(72) Inventors: James David Hughett, Sr., Monroe, GA (US); Salvatore Privitera, Mason, OH (US); Michael D. Hooven, Cincinnati, OH (US)

(73) Assignee: AtriCure, Inc., Mason, OH (US)

( * ) Notice: Subject to any disclaimer, the term of this patent is extended or adjusted under 35 U.S.C. 154(b) by 251 days.

(21) Appl. No.: 17/958,347

(22) Filed: Oct. 1, 2022

(65) Prior Publication Data

US 2023/0023804 A1 Jan. 26, 2023

Related U.S. Application Data

(63) Continuation of application No. 15/874,257, filed on Jan. 18, 2018, now Pat. No. 11,471,161, which is a continuation of application No. 14/462,930, filed on Aug. 19, 2014, now Pat. No. 9,883,863, which is a continuation of application No. 13/010,509, filed on Jan. 20, 2011, now Pat. No. 8,852,218, which is a continuation of application No. PCT/US2009/051270, filed on Jul. 21, 2009.

(Continued)

(51) Int. Cl.
*A61B 17/12* (2006.01)
*A61B 17/08* (2006.01)
*A61B 17/122* (2006.01)
*A61B 17/128* (2006.01)

(52) U.S. Cl.
CPC .... *A61B 17/12022* (2013.01); *A61B 17/1227* (2013.01); *A61B 17/1285* (2013.01); *A61B 17/08* (2013.01); *A61B 2017/1205* (2013.01)

(58) Field of Classification Search
None
See application file for complete search history.

(56) References Cited

U.S. PATENT DOCUMENTS 3,916,908 A * 11/1975 Leveen ............... A61B 17/122
 24/456
6,793,664 B2 * 9/2004 Mazzocchi ........ A61B 17/1285
 606/157

(Continued)

*Primary Examiner* — Shaun L David
(74) *Attorney, Agent, or Firm* — Dorton & Willis LLP; Ryan Willis

(57) ABSTRACT

Apparatus and methods are disclosed for occluding an anatomical structure including an occlusion apparatus having first and second beams and at least one connector for connecting the respective ends of the beams together. The occlusion apparatus may be adapted for use in a deployment device having a pair of jaws and optionally having a respective pair of shuttle bodies for releasably connecting an occlusion apparatus to the jaws while in an open position and for releasing the occlusion device from the jaws while in a closed position. A system for occluding an anatomical structure is also disclosed that includes an occlusion apparatus and a deployment device for holding the occlusion apparatus in an open position for locating the occlusion device adjacent the anatomical structure to be occluded and then moving the occlusion apparatus to a closed position and locking the occlusion apparatus in the closed position.

3 Claims, 14 Drawing Sheets

Related U.S. Application Data

(60) Provisional application No. 61/082,266, filed on Jul. 21, 2008.

(56) References Cited

U.S. PATENT DOCUMENTS

| | | | | |
|---|---|---|---|---|
| 7,691,053 | B2* | 4/2010 | Viola | A61B 17/08 606/151 |
| 7,862,571 | B2* | 1/2011 | Dennis | A61B 17/1227 606/143 |
| 7,892,244 | B2* | 2/2011 | Monassevitch | A61B 17/0643 606/151 |
| 2002/0183768 | A1* | 12/2002 | Deem | A61B 17/1114 606/151 |
| 2005/0149068 | A1* | 7/2005 | Williams | A61B 17/1227 606/151 |
| 2005/0149069 | A1* | 7/2005 | Bertolero | A61B 1/12 606/151 |
| 2005/0277959 | A1* | 12/2005 | Cosgrove | A61B 17/122 606/151 |
| 2006/0009793 | A1* | 1/2006 | Rennich | A61B 17/122 606/157 |
| 2006/0020271 | A1* | 1/2006 | Stewart | A61B 17/12013 606/139 |
| 2007/0213747 | A1* | 9/2007 | Monassevitch | A61B 17/122 606/151 |
| 2008/0033457 | A1* | 2/2008 | Francischelli | A61B 17/1285 606/157 |
| 2008/0039879 | A1* | 2/2008 | Chin | A61B 17/064 606/157 |
| 2009/0012545 | A1* | 1/2009 | Williamson, IV | A61B 17/1227 606/157 |
| 2009/0105753 | A1* | 4/2009 | Greenhalgh | A61L 17/145 606/228 |
| 2009/0209986 | A1* | 8/2009 | Stewart | A61B 17/122 606/157 |
| 2009/0240266 | A1* | 9/2009 | Dennis | A61B 17/1285 606/151 |
| 2010/0082050 | A1* | 4/2010 | Kassab | A61F 5/0086 606/157 |
| 2010/0114124 | A1* | 5/2010 | Kelleher | A61B 17/1227 606/151 |
| 2010/0145361 | A1* | 6/2010 | Francischelli | A61B 17/12009 606/139 |
| 2011/0046437 | A1* | 2/2011 | Kassab | A61F 5/0013 606/157 |
| 2011/0046641 | A1* | 2/2011 | Kassab | A61F 5/0086 606/139 |
| 2011/0190791 | A1* | 8/2011 | Jacobs | A61B 17/1285 606/139 |
| 2012/0035631 | A1* | 2/2012 | Hughett, Sr. | A61B 17/1227 606/157 |
| 2012/0109161 | A1* | 5/2012 | Privitera | A61B 17/1285 29/428 |
| 2012/0123445 | A1* | 5/2012 | Hughett, Sr. | A61B 17/1227 24/485 |

* cited by examiner

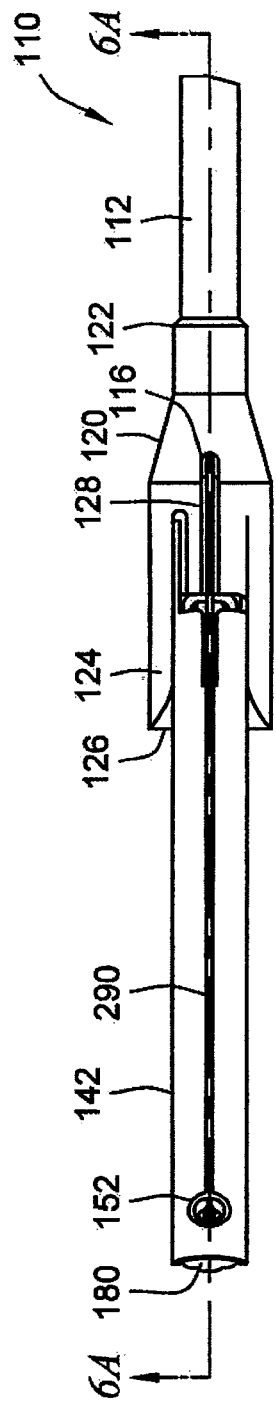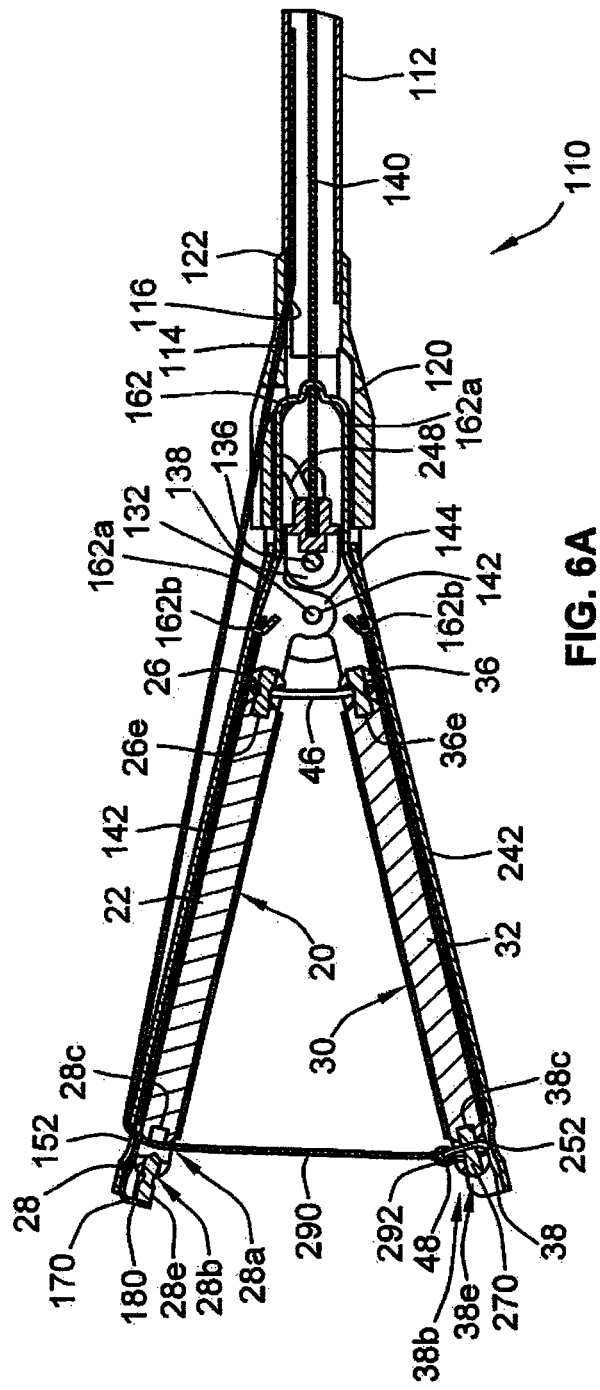

APPARATUS AND METHODS FOR OCCLUDING AN ANATOMICAL STRUCTURE

CROSS-REFERENCE TO RELATED APPLICATIONS

This application is a continuation of and claims priority under 35 U.S.C. § 120 to U.S. patent application Ser. No. 15/874,257 filed on Jan. 18, 2018 and titled, "APPARATUS AND METHODS FOR OCCLUDING AN ANATOMICAL STRUCTURE," now U.S. Pat. No. 11,471,161, which was a continuation of U.S. patent application Ser. No. 14/462,930 filed on Aug. 19, 2014, entitled, "APPARATUS AND METHODS FOR OCCLUDING AN ANATOMICAL STRUCTURE," now U.S. Pat. No. 9,883,863, which was a continuation of U.S. patent application Ser. No. 13/010,509 filed on Jan. 20, 2011, entitled, "APPARATUS AND METHODS FOR OCCLUDING AN ANATOMICAL STRUCTURE," now U.S. Pat. No. 8,852,218, which claimed priority to Patent Cooperation Treaty Application Serial No. PCT/US09/51270 filed on Jul. 21, 2009, entitled, "APPARATUS AND METHODS FOR OCCLUDING AN ANATOMICAL STRUCTURE," which claimed priority to U.S. Provisional Patent Application Ser. No. 61/082,266, entitled, "APPARATUS AND METHODS FOR OCCLUDING AN ANATOMICAL STRUCTURE," filed Jul. 21, 2008, the disclosures of which are hereby incorporated by reference.

RELATED ART

This disclosure relates generally to devices and methods that may be used to clamp tissue or occlude an anatomical structure. For example, it may be desirable to occlude an anatomical structure such as the left atrial appendage (LAA). It will be appreciated that blood may otherwise tend to clot in a non-occluded LAA, which may increase the risk of stroke. Occlusion of the LAA may prevent blood from entering the LAA, thereby preventing blood from clotting in the LAA. Such occlusion may therefore also prevent blood clots from exiting the LAA into the blood stream, such that the risk of stroke may be reduced.

Of course, there may be other purposes for occluding the LAA, and there are a variety of other anatomical structures that may be clamped or occluded. Due to the varying dimensions of the LAA and other anatomical structures between individuals, it will be appreciated that it may be desirable to provide occlusion devices of varying dimensions and/or configurations to correspond to the particular anatomical structure intended to be occluded or for other purposes.

INTRODUCTION TO THE INVENTION

The present disclosure generally presents apparatus and methods for use in clamping tissue or occluding anatomical structures. An apparatus is provided that comprises a pair of elongated clamping members, each having first and second ends. An elastic connector is provided that extends between at least the first ends of the clamping members and is operably associated with each of the clamping members such that the tension applied by the elastic connector moves the clamping members from a spaced apart position to receive tissue therebetween toward each other to clamp tissue. More specifically, an apparatus is provided for occluding an anatomical structure where the apparatus includes a first beam member having first and second ends and a second beam member having first and second ends. At least a first resilient or elastic member connects the first beam member and the second beam member to apply a force to the beam members sufficient to cause the beam members to occlude an anatomical structure held between the beam members.

In a specific embodiment, the first resilient/elastic member is an elastic band connected to the first end of the first beam member and is connected to the first end of the second beam member. The apparatus further includes at least a second resilient/elastic member that is connected to the second end of the first beam member when the occlusion apparatus is in an open position and where the second resilient member is stretched to facilitate connection to the second end of the second beam member when the occlusion apparatus is in a closed position.

In a second aspect, a system for occluding an anatomical structure is provided which includes an occlusion apparatus and a deployment device. The deployment device is adapted to hold the occlusion apparatus in an open position for locating the occlusion apparatus adjacent an anatomical structure to be occluded. The deployment device also includes a primary mover adapted to move the occlusion apparatus to a closed position and a secondary mover adapted to lock the occlusion apparatus in the closed position.

In yet another aspect, a deployment device for applying an occlusion apparatus to an anatomical structure is provided. The deployment device includes a shaft having a distal end, first and second jaws coupled to the distal end of the shaft and biased toward an open position, as well as first and second shuttle bodies slidably connected to the respective first and second jaws. The first and second shuttle bodies are adapted to releasably connect the occlusion apparatus to the respective first and second jaws when the first and second shuttle bodies are in a first position relative to the first and second jaws. The deployment device further includes the jaws being movable to a closed position after which the shuttle bodies are movable to a second position relative to the first and second jaws and the occlusion apparatus is released from the deployment device.

BRIEF DESCRIPTION OF THE DRAWINGS

The present disclosure includes the following description of certain examples taken in conjunction with the accompanying drawings, in which like reference numerals identify the same elements and in which:

FIG. 6 depicts an upper view of the example deployment device of FIG. 3 having the example apparatus of FIG. 1 positioned therein;

FIG. 6A depicts a cross-sectional view through section line A-A of the structures of FIG. 6, while in an open position;

DETAILED DESCRIPTION

Figure 1:
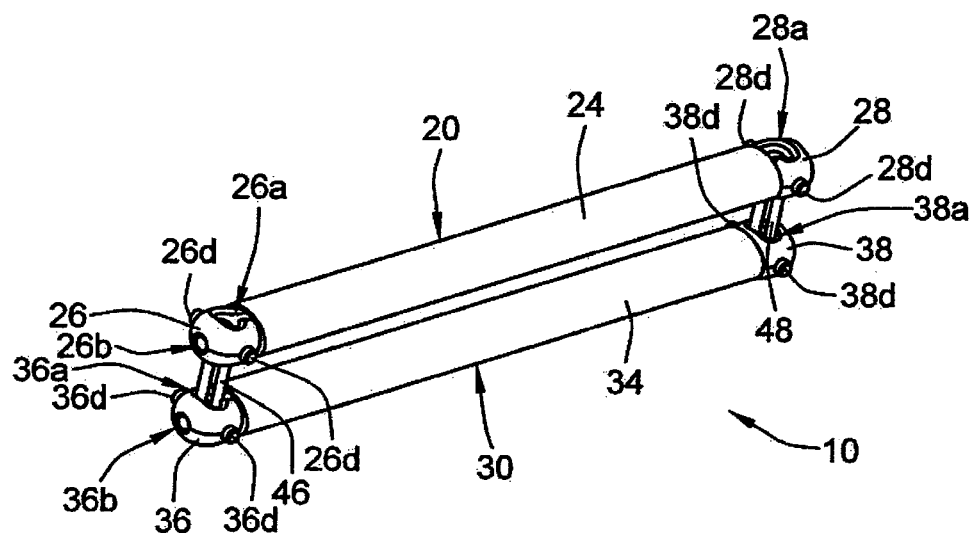
FIG. 1 depicts a perspective view of an example apparatus for occluding an anatomical structure, in a closed position but with the beam members shown in a stretched apart configuration to facilitate viewing and description herein.

Although the following discloses example apparatus and methods for use in occluding anatomical structures, it will be understood by one of ordinary skill in the art that the teachings of this disclosure are in no way limited to the example shown. On the contrary, it is contemplated that the teachings of this disclosure may be implemented in alternative configurations and environments. For example, although the example apparatus described herein is described in conjunction with a configuration for occluding an LAA, those of ordinary skill in the art will readily recognize that the example apparatus and methods may be used to occlude other anatomical structures and may be configured to correspond to such other structures as needed. Accordingly, while the following describes an example apparatus and methods of use thereof, persons of ordinary skill in the art will appreciate that the disclosed example is not the only way to implement such apparatus and/or methods, and the drawings and descriptions should be regarded as illustrative in nature and not restrictive.

It will be appreciated that the example of an occlusion apparatus may act as a clamp or clip. For instance, as will be described in greater detail below, an occlusion apparatus may be secured to an anatomical structure. To the extent that such an anatomical structure would otherwise permit communication of fluid through the anatomical structure, the clamping or other engagement of an occlusion apparatus on the anatomical structure may substantially prevent the communication of fluid through, into, or out of the anatomical structure. The following example of an occlusion apparatus may therefore be used to form an occlusion in the anatomical structure. It will be appreciated, however, that an occlusion apparatus need not necessarily be used to form a complete occlusion in an anatomical structure, and may be instead used simply to restrict or regulate the flow of fluid through, into, or out of an anatomical structure.

In addition, it will be appreciated that the following example of an occlusion apparatus may be configured such that it is atraumatic with regard to the anatomical structure being occluded, adjacent organs, and/or adjacent tissue. Due to the varying dimensions of the LAA and other anatomical structures between individuals, it will be appreciated that the overall dimensions or configurations of an occlusion apparatus may be varied to accommodate anatomical structures of different dimensions or for other purposes.

The example occlusion apparatus may include a sock or retention material configured to enshroud at least some of the components. A sock may comprise a knit, braided polyester material. Of course, any other suitable materials may be used for a sock, including but not limited to polyethylene. It will also be appreciated that a sock is optional and may be configured to provide friction and to facilitate the growth of scar tissue to hold the occlusion apparatus adjacent the anatomical structure. A sock may also be sutured to tissue to further secure an occlusion apparatus in place. At least one manner in which a sock may be incorporated in the example occlusion apparatus and associated methods is described in more detail below. However, it will become apparent to those of ordinary skill in the art that components of an occlusion apparatus may be provided with a coating, textured or perforated surface, or some other configuration may be used to provide retention results similar to those provided by a sock. As one example, ionic plasma deposition (IPD), such as is available from Chameleon Scientific of Plymouth MN, may be employed to create a surface-engineered nanostructure coating on components to enhance adhesion and scar tissue growth. Molecular plasma deposition of colloidal materials onto metal or non-metal surfaces to affect biological activity also is discussed in U.S. Pat. No. 7,250,195, incorporated herein by reference.

Turning to the drawings, FIGS. 1-10 illustrate one specific example of an occlusion apparatus 10, a use for such an occlusion apparatus 10, and a deployment device 110 for manipulating and placing the occlusion apparatus 10 in position on an anatomical structure to be occluded.

As is described in greater detail below, the occlusion apparatus generally comprises a pair of elongated beam members whose ends are connected to each other by one or more elastic or resilient members, or other closure element, that apply a force to the first and second beam members sufficient for the beam members to occlude an anatomical structure held between the beam members. FIGS. 11A-C, 12A-E, and 13A-E show alternative configurations by which the resilient member may be attached to the beam members. FIGS. 14A-D, 15A-C and 16A-B show alternative configurations for the beams for facilitating attachment of the resilient members. FIGS. 17A-C, 13A-D and 19A-E show alternative configurations for the resilient member/closure element. As can be appreciated by one skilled in the art, the various configurations for these aspects of the occlusion apparatus can be combined in various combinations to achieve an occlusion apparatus in accordance with this disclosure.

Returning to FIGS. 1-10, FIG. 1 shows a view of the example occlusion apparatus 10 in a closed but stretched position for ease of viewing and description, while FIG. 2 shows the occlusion apparatus installed on a representation of a left atrial appendage LAA of a patient's heart. The representation of the left atrial appendage LAA is a simplified rendering showing the left atrial appendage in a position extending outward from the left atrium of a heart. With an occlusion apparatus 10 held by a deployment device 110, the occlusion apparatus 10 may be moved to an open position, to allow a portion of the LAA to be passed through the open occlusion apparatus 10, for positioning of the occlusion apparatus 10 adjacent to the outside of the LAA. With the occlusion apparatus 10 so positioned, the deployment device 110 may be used to move the occlusion apparatus 10 to a closed position and to release the occlusion apparatus 10.

FIG. 1 shows the occlusion apparatus 10 having a pair of beam members 20, 30. Each beam member 20, 30 has a central body 22, 32, respectively. Each beam member 20, 30 further has a first end 26, 36, respectively. The first ends 26, 36 are represented as being the proximal ends of beam members 20, 30 with respect to the deployment device 110, as best seen for example in FIGS. 3 and 6A. Similarly, each beam member 20, 30 also has a second end 28, 38, respectively, with the second ends 28, 38 being the respective distal ends of beam members 20, 30 with respect to the deployment device 110. In the example configuration shown in FIGS. 1-10, each beam member 20, 30 has its body 22, 32 and its respective first and second ends 26, 28 and 36, 38 integrally formed, such as by molding of medical grade plastics. It will be appreciated that alternatively, the first and/or second ends may be separate components formed by any suitable manufacturing methods and may be joined to the central bodies in any suitable manner.

The beam members 20, 30 are shown in this example as being covered by a sock 24, 34, respectively. Each example sock 24, 34 is formed in a tubular manner and slid into position over the respective central body 22, 32, as seen for example in FIG. 9 which includes a cross-sectional view of a portion of the central body 32 and an end 38 of the beam member 30. Each sock 24, 34 may be formed of a material as above described, so as to enhance retention of the occlusion apparatus 10 when installed on an anatomical structure. It will be appreciated that the example socks 24, 34 are optional, may be formed and applied in alternative suitable manners, or that alternative retention structures or coatings may be used to enhance the ability of tissue growth adjacent an installed occlusion apparatus 10 to assist in holding the occlusion apparatus 10 in place.

In this example, the ends 26, 28, 36, 38 of the occlusion apparatus 10 are shown as having a common configuration. Each end 26, 28, 36, 38 has a first passageway 26a, 28a, 36a, 38a, respectively, therethrough in an orientation that is perpendicular to a longitudinal axis of the respective beam member 20, 30. The first passageways 26a, 28a, 36a, 38a also are oriented so as to run from an upper side to a lower side of each respective end. Each end 26, 28, 36, 38 further includes a second passageway 26b, 28b, 36b, 38b, respectively, passing through the center of the face of the respective end 26, 28, 36, 38 and extending into a coaxial seat 26c, 28c, 36c, 38c, respectively, within the central body 22, 32 of the beam members 20, 30, best seen in FIGS. 6A and 9. Each seat 26c, 28c, 36c, 38c is open to a respective first passageway 26a, 28a, 36a, 38a, such that the second passageways 26b, 28b, 36b, 38b are oriented perpendicular to and effectively pass through the respective first passageways 26a, 28a, 36a, 38a. Each end 26, 28, 36, 38 also has a pair of protrusions 26d, 28d, 36d, 38d, respectively, extending outward therefrom in an orientation perpendicular to the first passageways 24a, 26a, 34a, 36a.

The respective ends 26, 28, 36, 38 each carry a pin 26e, 28e, 36e, 38e that is received within the respective second passageway 26b, 28b, 36b, 38b, and may be received within the respective seat 26c, 28c, 36c, 38c. The pins 26e and 36e disposed at the first ends 26, 36 may be used to connect the beam members 20, 30 to a first resilient/elastic member or band 46. First band 46 is formed as a closed loop having a central opening, such as an O-ring, and may be formed of a rubber or other suitable elastomeric material. As best seen in FIG. 6A, the pins 26e and 36e are positioned within respective second passageways 26b, 36b and are advanced into respective seats 26c, 36c. In this position, each pin 26e, 36e traverses a first passageway 26a, 36a and the central opening of the band 46, thereby achieving a connection between the first ends 26, 36 that permits some flexibility in relative movements while also resiliently biasing the first ends 26, 36 toward each other, as will be discussed in greater detail herein.

The pins 28e and 38e are disposed at the second ends 28, 38, which are located distally relative to the deployment device 110. The pins 28e and 38e similarly may be used to connect the beam members 20, 30 to a second resilient/elastic member or band 48. The second band 48 preferably is formed in a like manner to the first band 46. Thus, the second band 48 also is formed of an elastomeric material in a closed loop having a central opening.

In the example occlusion apparatus 10, when in an open position, as shown in FIG. 6A, the second ends 28, 38 are not connected to each other by the second band 48 and the pins 28e and 38e. The band 48 is indeed connected to the second end 38 of the beam member 30 by pin 38e which is positioned within the respective second passageway 38b, extends through the central opening in the second band 48, and is advanced into respective seat 38c. However, at the second end 28 of beam member 20, the pin 28e is positioned within the respective second passageway 28b but does not extend through the central opening in the second band 48, and is not advanced into the respective seat 28c. Thus, with the occlusion apparatus 10 in an open position, the second band 48 is not bound by the pin 28e and the second ends 28, 38 are permitted a greater range of motion than the first ends 26, 36.

Figure 2:
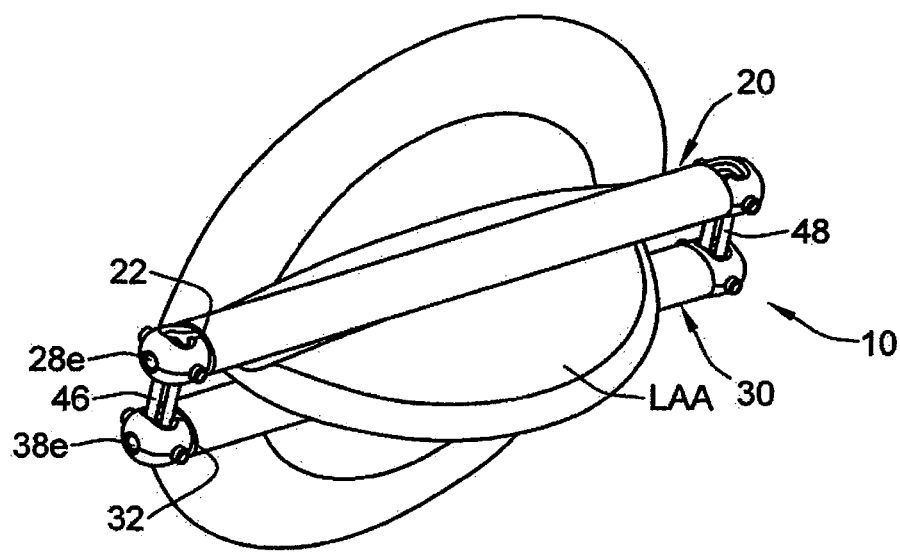
FIG. 2 depicts the example apparatus of FIG. 1 applied to an anatomical structure.
Figure 3:
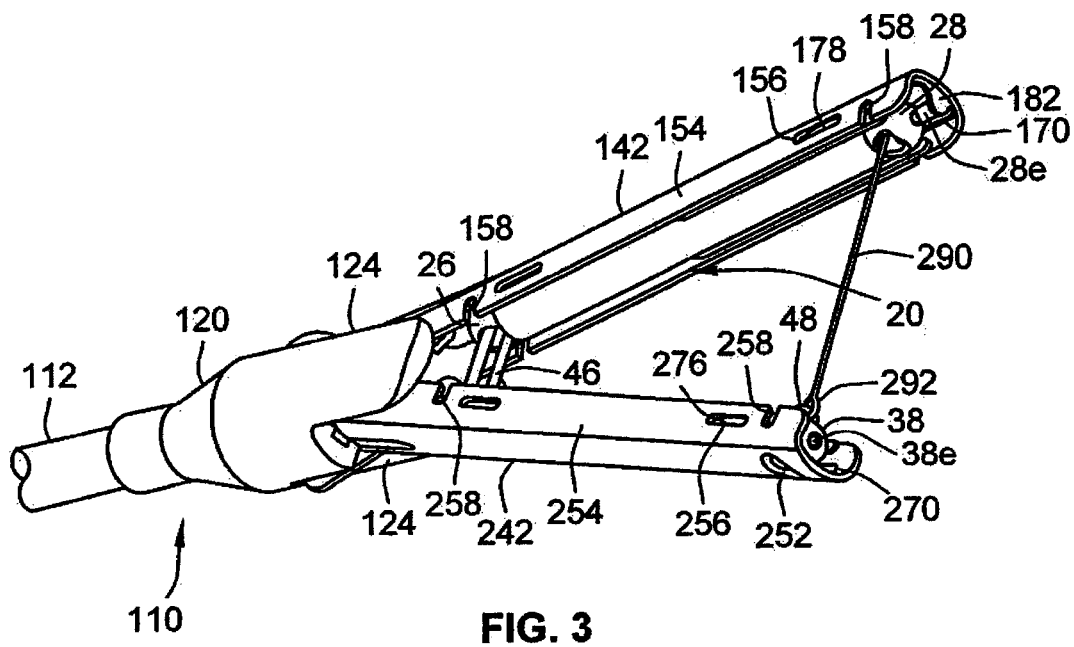
FIG. 3 depicts a perspective view of the example apparatus of FIG. 1, held in an open position within an example deployment device.
Figure 4:
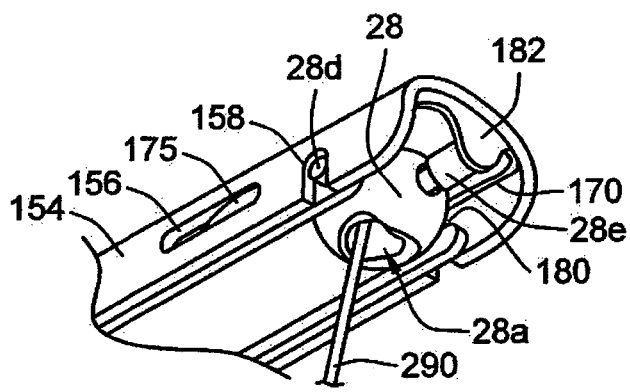
FIG. 4 depicts a closer perspective view of the distal end of an upper member of the example apparatus of FIG. 1 within the example deployment device of FIG. 3.
Figure 5:
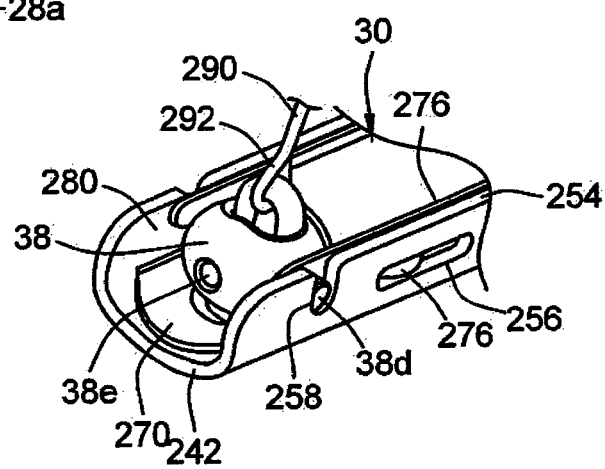
FIG. 5 depicts a closer perspective view of the distal end of a lower member of the example apparatus of FIG. 1 within the example deployment device of FIG. 3.
Figure 10:
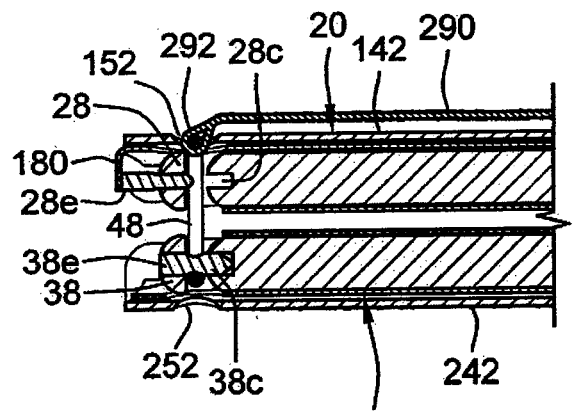
FIG. 10 depicts a cross-sectional view of the distal ends of the example apparatus in a closed position while held within the example deployment device.

As will be described in greater detail below, the example occlusion apparatus 10 is able to achieve a broad open position to assist in capturing the anatomical structure to be occluded, such as shown in FIGS. 3 and 6A, while also providing a very controlled clamping load and operating range when in a closed position, such as shown in FIG. 2. Accordingly, in addition to the relatively greater range of motion in the open position, the second ends 28, 38 of the beam members 20, 30 may be moved toward a closed position and the second band 48 may be drawn into a position that permits the pin 28e to be selectively advanced through the central opening in the second band 48 and into the respective seat 28c, thereby connecting the second ends 28, 38, as best seen in FIG. 10.

When in the closed position, as shown in FIG. 2, it is preferable to have the bands 46, 48 exert a comparable force to achieve a relatively parallel application of pressure by the beam members 20, 30. Thus, equivalent and appropriate static or unstretched length, working or stretched length, and resiliency for the bands 46, 48 may be chosen depending on the desired application of the occlusion apparatus 10. For instance, when used for occlusion of a left atrial appendage, it may be desirable to select bands 46, 48 which have an effective working length beyond their static length which permits approximately 4 mm of travel between the beam members 20, 30, while having resiliency characteristics that permit an operating range of 2-12 psi for the clamping load of the occlusion apparatus 10. Due to the configuration of occlusion apparatus 10 in this particular example, the exerted pressure may be substantially uniform along the length of the occlusion device 10. Of course, it will be appreciated that occlusion device 10 may be configured to exert any other suitable amount of travel and pressure. In addition, occlusion device 10 may be configured such that the pressure exerted by the occlusion device 10 is not substantially uniform along its length.

In the present example, the clamping load or pressure exerted by the closed occlusion apparatus 10 on the left atrial appendage LAA in FIG. 2 results in occlusion apparatus 10 creating an occlusion of the LAA by clamping the LAA, thereby preventing blood from entering or leaving the LAA relative to the left atrium of the heart. Accordingly, those of ordinary skill in the art will appreciate that occlusion apparatus 10 may be used in a remedial or prophylactic fashion, particularly for reducing the risk of stroke by preventing the formation of blood clots in the left atrial appendage LAA of a patient. It will be appreciated that the use of occlusion apparatus 10, as illustrated in FIG. 1, and as described above, is merely exemplary, and that an occlusion apparatus 10 may be used in a variety of different ways and with a variety of different anatomical structures.

If occlusion apparatus 10 is left in the position and configuration shown in FIG. 2 for a substantial period of time, the LAA may simply atrophy and wither away. In the meantime, the occlusion apparatus 10 may essentially become ingrown with scar tissue, which may be aided by the use of socks 24, 34, or other suitable tissue retention structures or coatings. Various other suitable uses will be apparent to those of ordinary skill in the art.

Turning to the interaction between the occlusion apparatus 10 and the deployment device 110, it will be appreciated from FIGS. 3-7 that the deployment device is used to position an occlusion apparatus 10 in an open position around an anatomical structure to be occluded, and then is used to move the occlusion apparatus 10 to a closed position and to deploy the occlusion apparatus 10 to permit the deployment device 110 to be removed from the patient. The example deployment device 110 includes a hollow shaft 112 having a distal end 114 that includes a notch 116. The distal end 114 of the shaft 112 is connected to a hollow coupling head 120 at a proximal first end 122, such as by snap fit, or use of adhesives or other suitable fastening methods. The coupling head 120 has a pair of arms 124 terminating in a distal second end 126, and a groove 128 along a top side of coupling head 120. The shaft 112 and coupling head 120 may be formed of suitable relatively rigid medical grade metals, plastics, or the like.

Figure 7:
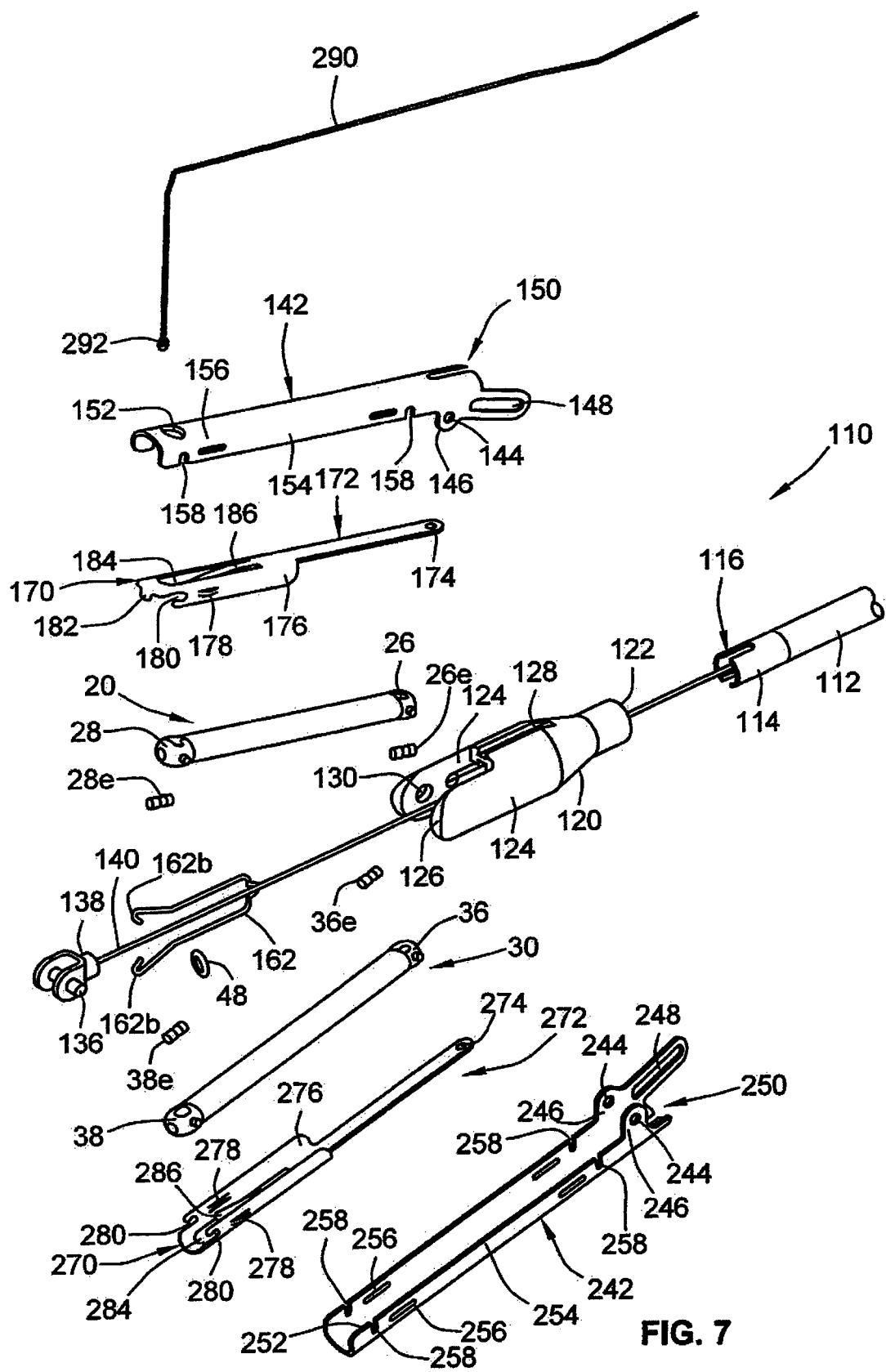
FIG. 7 depicts a perspective exploded view of the example apparatus for occluding an anatomical structure and the example deployment device for use therewith.

Each arm 124 of the example deployment device apparatus 110 includes a recess 130 that receives a pivot pin 132, and a slot 134 that receives a sliding pin 136, best seen in FIG. 7. The sliding pin 136 extends outward from a fitting 138 that is connected to the distal end of a cable 140 that runs through the hollow coupling head 120 and shaft 112 and is connected at its proximal end to an operator control handle (not shown). The fitting 138 may be formed of suitable medical grade metals or plastics, or the like. It will be appreciated that cable 140 may be formed of a single strand or multiple strands of suitable metal or plastic wire, or the like.

As best seen in FIGS. 6A and 7, the pivot pin 132 that is held in the recesses 130 of arms 124 also engages an upper jaw 142 as it passes through apertures 144 on side tabs 146, and engages an opposed lower jaw 242 as it passes through apertures 244 on side tabs 246. Opposed upper and lower jaws 142, 242 may be constructed of suitable relatively rigid medical grade metals, plastics, or the like. One of the side tabs 146, 246 of each jaw 142, 242 includes a slot 148, 248 that engages the sliding pin 136 as the sliding pin 136 passes through the slot 148, 248. It will be appreciated that as the cable 140 is drawn through the coupling head 120 and the shaft 112 of the deployment device 110, the fitting 138 is moved in a direction toward the proximal first end 122 of the coupling head 120, and as a result, the sliding pin 136 is moved within the slots 134 in the arms 124 of the coupling head 120 toward the proximal first end 122 of the coupling head 120. As the sliding pin 136 moves proximally within the slots 134 in the arms 124 of the coupling head 120, the sliding pin 136 also slides within the slot 148 in the upper jaw 142 and within the slot 248 within the lower jaw 242. Given the angles of the slots 148, 248 in the jaws 142, 242, respectively, the movement of the sliding pin 136 in the proximal direction can be used to force the jaws 142, 242 to hinge about the hinge pin 132 toward a closed position.

The opposed jaws 142, 242 also include a notch 150, 250 near their proximal ends, an aperture 152, 252 near their distal ends, and sides 154, 254. The sides 154, 254 of the jaws 142, 242 have slots 156, 256 parallel to the length of the jaws 142, 242, and notches 158, 258 that are perpendicular to the length of the jaws 142, 242 and that are open toward the respective opposed jaw. The use and significance of these notches 150, 250, slots 156, 256, and notches 158, 258 will be discussed below in more detail after introduction of further cooperative components.

Figure 8:
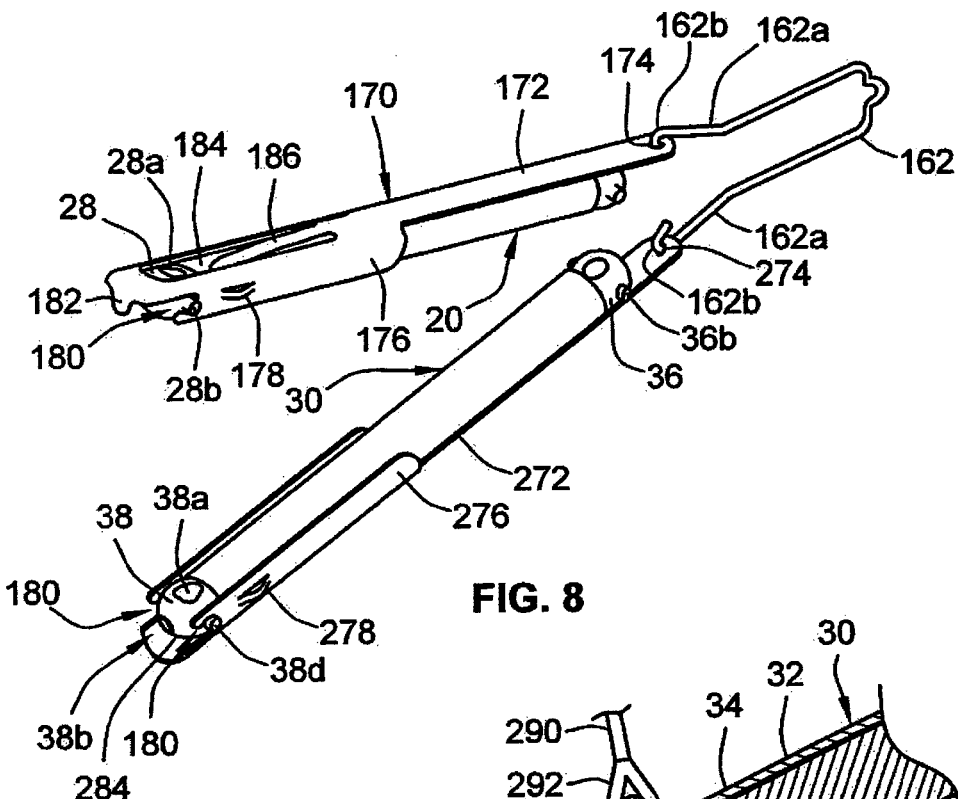
FIG. 8 depicts a perspective view of a portion of the example apparatus of FIG. 1 seated within a portion of the example deployment device of FIG. 3.

As best seen in FIGS. 7 and 8, a shuttle assembly 160 includes an upper shuttle body 170, a lower shuttle body 270 and a retainer 162. FIG. 8 shows the shuttle assembly 160 in a simplified form for ease of viewing, for instance without the bands 46, 48, and without being connected to cable 140, as shown in FIG. 7. Each upper and lower shuttle body 170, 270 has an elongate portion 172, 272 with an aperture 174, 274 at a proximal end of the shuttle body 170, 270. Each shuttle body 170, 270 also includes generally upstanding sides 176, 276, each of which has a small protrusion 178, 278 that extends outward from and parallel to the upstanding sides 166. The distal end of each shuttle body 170, 270 includes a notch 180 in each side 176, 276, and the upper shuttle body 172 further includes a tab 182 which is perpendicular to but upstanding like the sides 176. The elongate portion 172, 272 of each shuttle body 170, 270 also includes an elongated aperture 184, 284 with a biasing finger 186, 286 formed as a peninsula within the aperture 184, 284 and bent slightly inward toward the opposed shuttle body.

Figure 9:
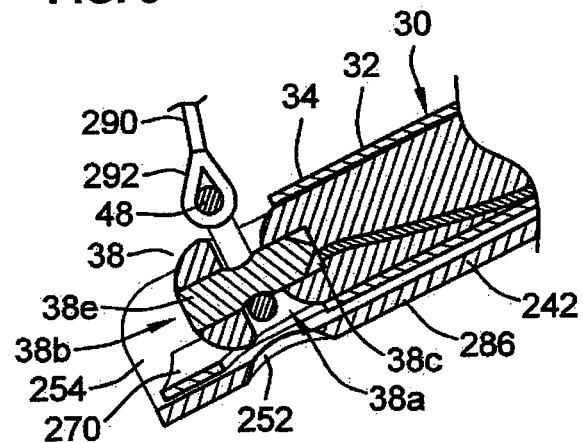
FIG. 9 depicts a cross-sectional view of the distal end of the example apparatus in an open position while held within the example deployment device.

In FIG. 8, the shuttle assembly 160 is shown with the upper shuttle body 170 receiving beam member 20 and lower shuttle body 270 receiving beam member 30. It will be appreciated that in loading the beam member 20 into the upper shuttle body 170 the beam member 20 must be placed between the sides 176 and pressed against the finger 186 until the protrusions 28*d* on the end 28 of the beam member 20 are aligned with the notches 180 of the upper shuttle body 170. The beam member 20 then must be moved in the proximal direction to seat the protrusions 28*d* in the notches 180 of the upper shuttle body 170. Similarly, in loading the beam member 30 into the lower shuffle body 270 the beam member 30 must be placed between the sides 276 and pressed against the finger 286 until the protrusions 38*d* on the end 38 of the beam member 30 are aligned with the notches 280, such that the beam member 30 may be moved proximally to seat the protrusions 38*d* in the notches 280 of the lower shuttle body 270. Note that the portion of the biasing finger 286 shown in FIG. 9 would not normally be in the position shown when the beam member 30 is loaded in the shuttle body 270. Rather the biasing finger 286 would be pushed to a position generally in alignment with the elongate portion 272 of the shuttle body 270. Accordingly, the portion of the biasing finger 286 is shown in FIG. 9 merely to illustrate the position of the biasing finger 286 relative to the shuttle body 270 and jaw 242 when a beam member 30 is not present.

FIG. 8 also shows the upper and lower shuttle bodies 170, 270 being connected at their proximal ends to the spring arms 162*a* at hook ends 162*b* via the apertures 174, 274. When the shuttle assembly 160 is installed within the jaws 142, 242, the spring arms 162*a* of the retainer 162 tend to bias the jaws 142, 242 toward an open position. With the retainer 162 connected to the cable 140, as shown in FIG. 7, it will be appreciated that movement of the shuttle assembly 160 in the proximal direction can be controlled by drawing the cable 140 in the proximal direction via an operator control handle (not shown).

A more complete view of the occlusion apparatus 10 loaded within the deployment device 110 and in an open position is shown in FIG. 6A and can be further appreciated in conjunction with FIGS. 7 and 8. Thus, when the upper and lower beam members 20, 30 are loaded within the upper and lower shuttle bodies 170, 270, the protrusions 28*d*, 38*d* are seated in the notches 180, 280 of the shuttle bodies 170, 270, as well as being seated in the notches 158, 258 of the upper and lower jaws 142, 242. In turn, it will be appreciated that the protrusions 178, 278 in the sides 176, 276 of the shuttle bodies 170, 270 are seated within the slots 156, 256 in the sides 154, 254 of the upper and lower jaws 142, 242. When the occlusion apparatus 10 is loaded in the deployment device 110, the band 46 is held by pins 26*e*, 36*e* at the proximal ends 26, 36 of beam members 20, 30, permitting some movement of beam members 20, 30 relative to each other. At the distal end 38 of the beam member 30, the pin 38*e* is installed through the opening in band 48. However, at the distal end 28 of beam member 20, pin 28*e* is not connected to the band 48. Instead, the pin 28*e* at the proximal end 28 of beam member 20 initially is located within the passageway 28*b*, but not advanced to the point of traversing the passageway 28*a*. With the beam members 20, 30 loaded in the deployment device 110, the arms 162*a* of the retainer 162 press outward against the jaws 142, 242 to hold the occlusion device 10 in an open position.

With the occlusion apparatus 10 loaded in the deployment device 110, as best seen in FIGS. 6 and 6A, a flexible cinching member 290 is connected at its distal end 292 to the band 48 that is connected to the pin 38*e* in the distal end 38 of the lower beam member 30. The cinching member 290 then is threaded upward through the passageway 28*a* in the end 28 of the beam member 20. The threading of flexible cinching member 290 then continues in the proximal direction through the groove 128 along the top side of the coupling head 120, then downward through the notch 116 in the shaft 112, and then within the shaft 112 to an operator control handle (not shown) at the proximal end of the deployment device 110. The flexible cinching member 290 preferably is a suture, but may be constructed of any suitable material(s) and in single or multiple filaments in the form of a thread, a string, a band, or any other suitable method or device.

With the beam members 20, 30 loaded within the shuttle assembly 160 and the jaws 142, 242, and with the jaws 142, 242 biased toward an open position by the arms 162*a* of the retainer 162, the distal end of the deployment device 110 can be moved into a position to locate between the beam members 20, 30 of the occlusion apparatus 10 an anatomical structure to be occluded. With the occlusion apparatus 10 appropriately positioned, the flexible cinching member 290 connected at its distal end 292 to the band 48 that is connected to the pin 38*e* in the distal end 38 of lower beam member 30 may then be drawn through the shaft 112 in the proximal direction. In this manner, the cinching member 290 may be used as a primary mover. Upon drawing the cinching member 290 in the proximal direction, the lower beam member 30 will be drawn toward opposed upper beam member 20. Given that the beam members 20, 30 have their protrusions 28*b*, 38*b* seated in the notches 180, 280 of upper and lower shuttle bodies 170, 270 and in the notches 158, 258 of the upper and lower jaws 142, 242, the jaws 142, 242 will be drawn toward a closed position, overcoming the bias provided by the arms 162*a* of the retainer 162.

As the beam members 20, 30 reach a closed position, the cinching member 290 may continue to be drawn in the proximal direction until the band 48 enters and is stretched into the first passageway 28*a* of the end 28 of the beam member 20 so as to traverse the second passageway 28*b* in the end 28 of the beam member 20. With the band 48 stretched into this position the motion of the cinching member 290 or primary mover is complete, and the cable 140 may be drawn in the proximal direction so as to move the sliding pin 136 of the fitting 138 within the slots 148, 248 in the jaws 142, 242. The movement of the sliding pin 136 in the proximal direction and against the angled slots 148, 248 tends to hold the jaws in a closed position.

As the cable 140 advances the sliding pin 136, it also moves the retainer 162 in the proximal direction. As the retainer 162 is moved in the proximal direction, the shuttle bodies 170, 270 also are moved in the proximal direction relative to the jaws 142, 242, however, the beam members 20, 30 do not move in the proximal direction due to the location of the protrusions 28*b*, 38*b* in the notches 152, 252 of the jaws 142, 242. The movement of the shuttle bodies 170, 270 in the proximal direction causes the tab 182 at the distal end of the upper shuttle body 170 to force the pin 28*e* to move in the proximal direction relative to the beam member 20. Thus, the tab 182 moves the pin 28*e* so as to traverse the first passageway 28*a* and extend through the opening in the stretched band 48 until the pin 28*e* comes to rest in the seat 28*c* within the central body 22 of beam member 20. As the shuttle bodies 170, 270 are moved in the proximal direction and the pin 28*e* is capturing the band 48 and being seated within the beam member 20, the notches 180, 280 in the sides 176, 276 of the shuttle bodies 170, 270 also are being moved in the proximal direction relative to the jaws 142, 242. This movement of the notches 180, 280 permits the protrusions 28*d*, 38*d* in the ends 28, 38 of the beam members 20, 30 to be released by the shuttle bodies 170, 270. Once the protrusions 28d, 38d are released by the notches 180, 280 of the shuttle bodies 170, 270, the protrusions are free to move out of the notches 152, 252 in the jaws 142, 242. By cutting the cinching member 290, the fingers 186, 286 in the shuttle bodies 170, 270 tend to urge the beam members 20, 30 to move away from the jaws 142, 242 to release the occlusion apparatus 10 from the deployment device 110. Thus, the cable 140 may be a secondary mover to move the shuttle bodies 170, 270 and therefore the pin 28e to lock the occlusion apparatus 10 in a closed position and to release it from the deployment device 110.

With the cinching member 290 cut and the retainer 162 continuing to bias the jaws 142, 242 toward an open position, the slots 148, 248 in the jaws 142, 242 tend to push the sliding pin 136 in a distal direction. Movement of the sliding pin 136 in the distal direction causes the cable 140 to be extended and the jaws 142, 242 to be moved toward an open position. Thus, by allowing the cable 140 to move in the distal direction, the jaws 142, 242 may achieve an open position to permit the occlusion apparatus 10 to completely disengage from the deployment device 110. With the occlusion apparatus 10 released by the jaws 142, 242, the deployment device 110 may be removed from the proximity of the occluded anatomical structure, leaving the occlusion apparatus 10 in position, such as is shown in FIG. 2.

In its closed position, the occlusion apparatus 10 includes a band 46, 48 at the respective ends 26, 36 and 28, 38 of the beam members 20, 30. The bands 46, 48 preferably have a similar resiliency and operating range over which they may be stretched, such that they will tend to apply an even pressure to the anatomical structure being occluded and thereby tend to maintain a parallel positioning of the beam members 20, 30. However, it will be appreciated that the bands 46, 48 need not be in the form of resilient loops and need not have equal elastomeric properties. Thus, it will be appreciated that other suitable configurations and materials may be used to permit resilient structures, generically referred to herein as a bands 46, 48 to permit stretching and connection to the beam members 20, 30. Moreover, while pins 26e, 28e, 36e and 38e and ends 26, 28, 36, 38 were shown as example structures by which the bands 46, 48 may be connected to the beam members 20, 30, it will be appreciated that alternative structures may be used to connect such resilient members to beam members, and that the same structures and materials need not be used at both ends of the pair of beam members.

In light of the foregoing, it will be appreciated that an example occlusion apparatus 10 may be transitioned from an open configuration toward a closed configuration by applying a pulling force to the cinching member 290, in the proximal direction. Once the band 48 that is connected to the cinching member 290 has been sufficiently stretched to move it into position for connection to a second beam member 20, then the shuttle bodies 170, 270 may be pulled in the proximal direction to simultaneously establish the connection of the band 28 to the beam member 20 while also disengaging the holding notches in the shuttle bodies 170, 270 from the protrusions 28d, 38d at the ends 28, 38 of the beam members. After cutting the cinching member 290, the cable 140 may be permitted to travel in the distal direction, which will allow the jaws 142, 242 to open to a point of fully releasing the beam members 20, 30. It will be appreciated that cinching member 290 may be drawn in the proximal direction and then permitted to extend, as needed, until the occlusion apparatus 10 is deemed to be appropriately positioned relative to the anatomical structure to be occluded, and ready for closure and deployment.

Figure 11A:
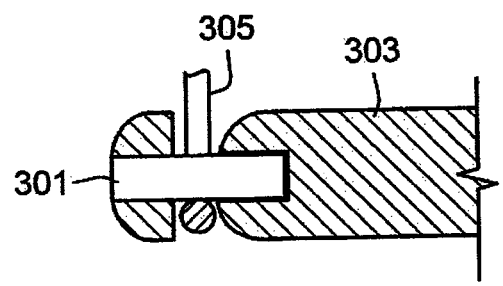
FIGS. 11A-C show three alternative configurations for affixing a resilient member to the end of a beam member.
Figure 11B:
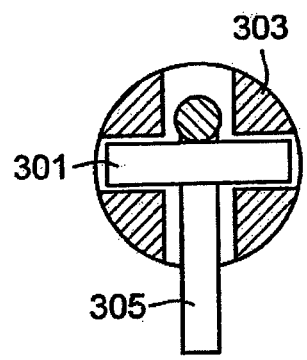

As noted above, various alternative means for attaching the resilient member or band to the beams may be employed. For example, in each of the embodiments 11A-C, a separate part or component is used to affix the resilient member to the beam. In FIGS. 11A and 11B, a pin 301 is received in the end of the beam member 303 to capture the resilient member 305. in FIG. 11A, the pin 301 is generally aligned with the longitudinal axis of the beam member 303 (as shown in described in greater detail in connection with the embodiment of FIGS. 1-10). Alternatively, as shown in FIG. 11B, the pin 301 can be oriented generally perpendicularly to the longitudinal axis of the beam member 303. Of course, other orientations for the pin would also be acceptable.

Figure 11C:
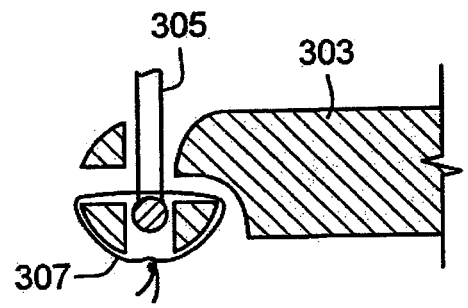

In a further alternative, a suture 307 may be used to secure the resilient member 305 to the beam 303, as shown in FIG. 11C. In FIG. 11C, the suture 307 is generally aligned with the longitudinal axis of the beam member 303. However, the suture may have other orientations.

Figure 12A:
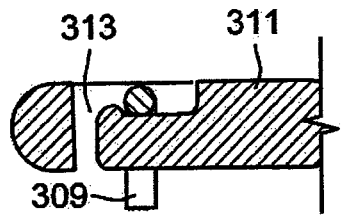
FIGS. 12A-E disclose five different configurations for attaching the resilient member to the beam member in which the attachment means is fixed to or part of the beam member.
Figure 12B:
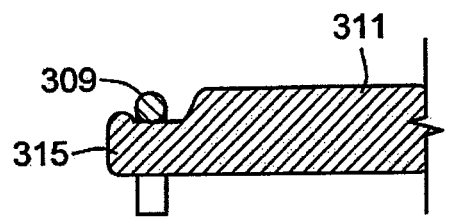
Figure 12C:
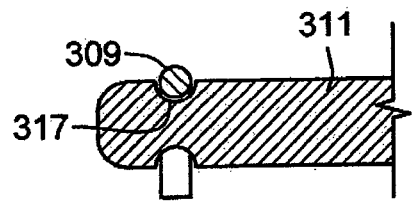
Figure 12D:
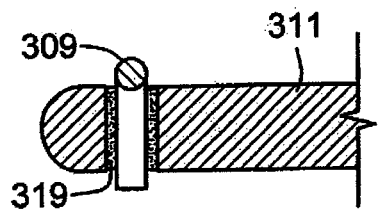
Figure 12E:
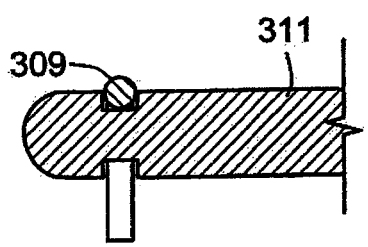
Figure 13A:
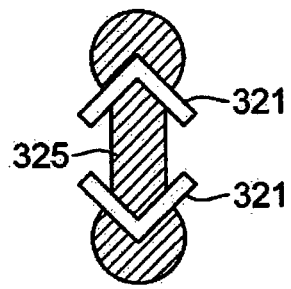
FIGS. 13A-E show five different configurations for securing the resilient member to the beam member in which the attachment means comprises a component fixed to the resilient member or is a part of the resilient member.
Figure 13B:
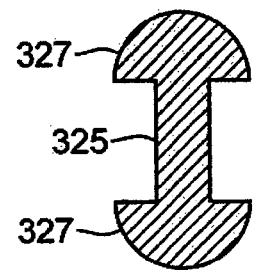
Figure 13C:
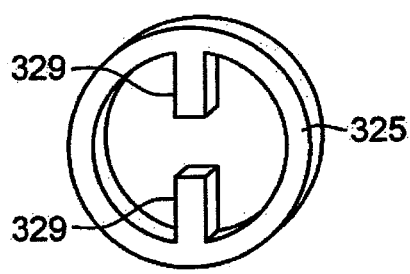
Figure 13D:
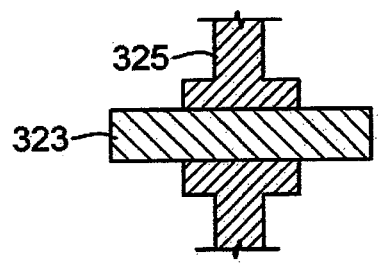
Figure 13E:
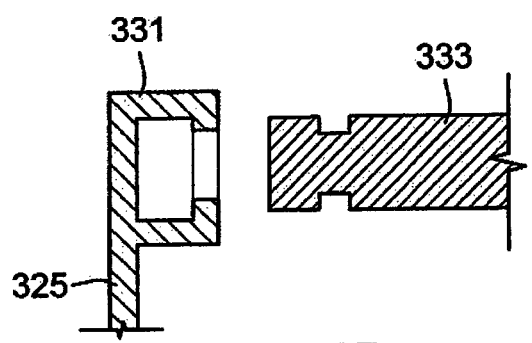

Alternatively, the component for affixing the resilient member to the beams may be fixed to, or integral with, the beam. In FIG. 12A, the attachment means for the resilient member 309 comprises an internal molded feature of the beam 311, such as a cantilevered post 313. In FIG. 12B, the beam 311 has an external molded feature, such as a relieved area or shoulder 315. As shown in FIG. 12C, the external feature may comprise a groove 317 that seats the resilient member 309. Alternatively, or additionally, the resilient member may be secured to the beam 311 by an adhesive or bonding agent 319, as illustrated in FIG. 12D. In a further alternative, the resilient member 309 may be insert molded to the beam 311, as represented by FIG. 12E.

In a further variation, the component for securing the resilient member to the beam member may be fixed to, or integral with, the resilient member. For example, a metallic component, such as a barb 321 (FIG. 13A) or a pin 323 (FIG. 13D), may be insert molded into the resilient member 325. Alternatively, the resilient member 325 can be molded to have opposed, enlarged heads 327 (FIG. 13B) or opposed pins 329 (FIG. 13C) that are adapted to be captured in a complementary structure on the beam. As a still further alternative, the resilient member may be molded with an end cap 331 (FIG. 13E) that fits over the end of a beam member 333 having a complementary shape.

Figure 14A:
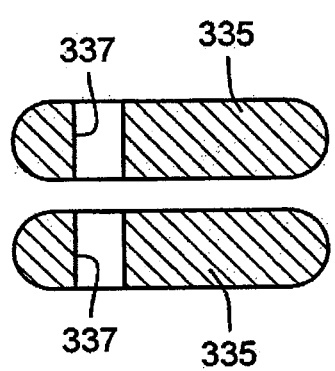
FIGS. 14A-D illustrate four different beam configurations for facilitating the attachment of the resilient member to the beam member by the creation of a window through the beam member.
Figure 14B:
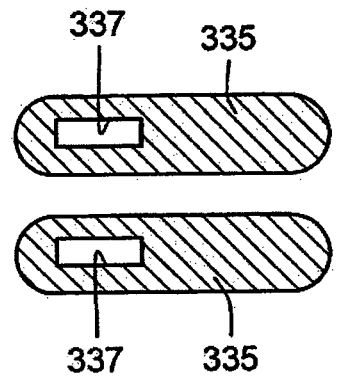
Figure 14C:
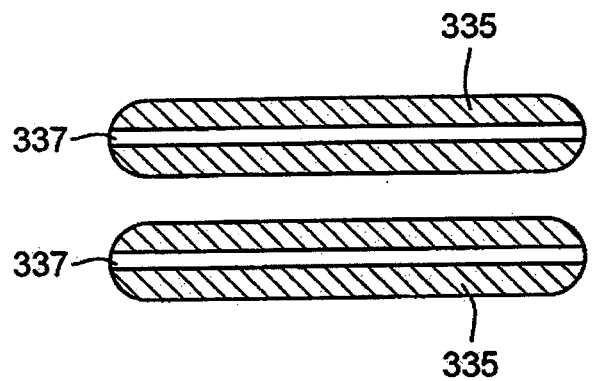
Figure 14D:
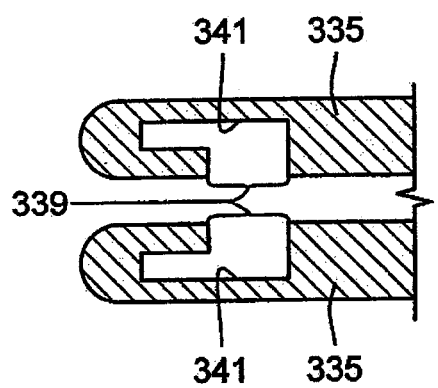

Various alternative configurations may also be employed for the attachment location on the beams for the resilient member or band. For example, in each of the embodiments of FIGS. 14A-D, the beams 335 are configured with a passageway or window 337 through the beam which receives the resilient member, or through which the resilient member may be threaded. In FIG. 14A, the windows 337 have a configuration that is generally perpendicular to the long axes of the beams 335, with the windows 337 being aligned so that they would also be generally perpendicular to an anatomical structure held therebetween. In FIG. 14B, the windows 337 are generally perpendicular to the long axes of the beams 335, with the windows being aligned so that they would also be generally parallel to an anatomical structure held therebetween. In FIG. 14C, the windows 337 are generally coincident with the long axes of the beams, and extend from end to end. FIG. 14D illustrates an embodiment similar to that shown in FIG. 14B, in which the windows 337 are oriented generally parallel to the anatomical structure. However, the beams are further relieved at 339 so that a keyhole-shaped pocket 341 is created.

Figure 15A:
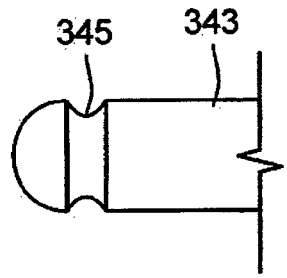
FIGS. 15A-C illustrate three different configurations of the ends of the beam members that facilitate the attachment of the resilient member thereto by wrapping the resilient member around the beam.
Figure 15B:
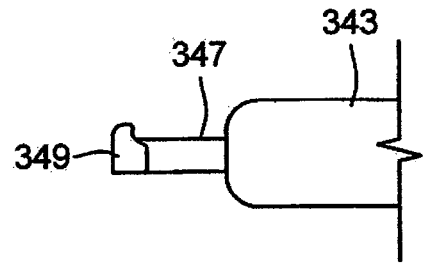
Figure 15C:
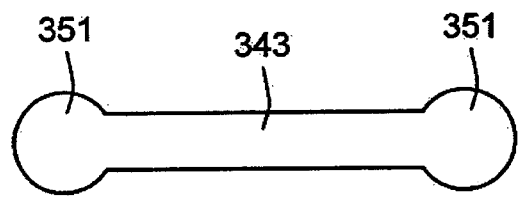

Alternatively, the attachment location on the beam may be configured so that the resilient member is looped or wrapped around the end of the beam. Turning to FIG. 15A, the end of the beam 343 may be provided with a radial groove 345 for seating the resilient member. In FIG. 15B, the beam 343 has a post 347 extending axially therefrom, the post having an enlarged end or hook 349 to help keep the resilient member seated on the post 347. In FIG. 15C, the beam 343 is provided with enlarged ends 351, so that it has a barbell appearance, for the same purpose.

Figure 16A:
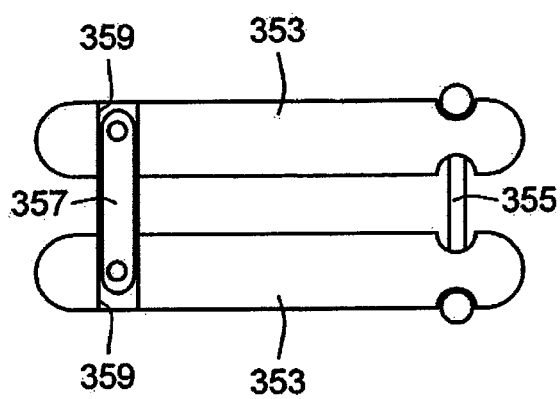
FIGS. 16A-B illustrate hybrid configurations of occlusion apparatus combining various of the configurations of FIGS. 14A-D and 15A-C.
Figure 16B:
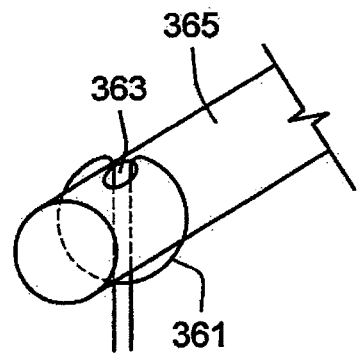

As can be readily appreciated, the various configurations of the attachment locations may be combined or mixed within a single occlusion apparatus. For example, as shown in FIG. 16A, the right ends of the beams 353 have their attachment location configured similar to that shown in FIG. 14A, with a through window for receiving the resilient band 355, while the left end is configured such that the resilient member 357 is wrapped or looped around the ends of the beams 353 and seated in a radial groove 359, similar to that shown in FIG. 15A. Of course, the configuration of the attachment location may be combined within each paired end of the occlusion apparatus such that a through window configuration is matched with a wrap-around configuration. A further hybrid is shown in FIG. 16B, where the resilient member 361 is threaded through the window 363 in the end of the beam 365 and then looped or wrapped around the end of the beam.

Figure 17A:
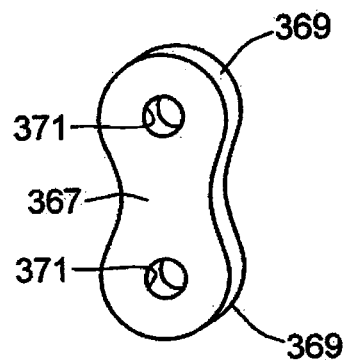
FIGS. 17A-C illustrate three different configurations for the resilient member in which the resilient member comprises a single element that is associated with each end of the beam members.
Figure 17B:
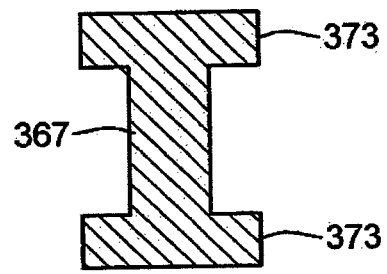
Figure 17C:
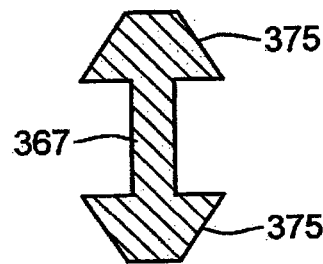

Various alternative configurations are also contemplated for the resilient/elastic member. As described above in connection with the embodiment of FIGS. 1-10, the resilient member may comprise a resilient O-ring. The resilient/elastic member may also be such as those shown in FIGS. 13A-B, described above. As a further alternative, the resilient member 367 may have a dog bone configuration with enlarged ends 369, as shown FIG. 17A, with a hole 371 in each end for affixing the band 367 to the beam. Further alternatives are shown in FIG. 17B, where the resilient member 367 has a barbell or I beam shape with enlarged ends 373, and FIG. 17C, where the enlarged ends 375 have a truncated conical shape, both of which would cooperate with a complementary shaped window on the beam. As a further alternative, two or more resilient members, such as any of those described above, may be affixed to each end of the beam set to achieve the desired closing force.

In each of the above-described embodiments, the occlusion apparatus has had at least one separate resilient member associated with each end of the beam set. It is also contemplated that a resilient member may be, if configured such that a single continuous resilient member is provided for each beam set, with the resilient member wrapping or extending axially around or through both beams.

Figure 18A:
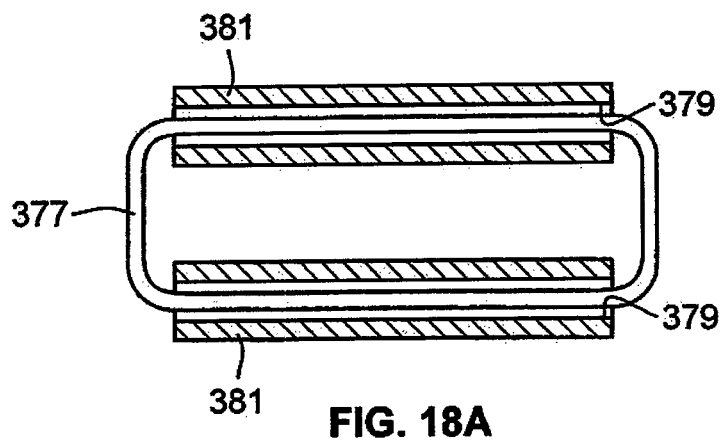
FIGS. 18A-D discloses four configurations in which the occlusion apparatus may additionally, or alternatively, include a single continuous resilient member that is associated with both beams of the occlusion apparatus.
Figure 18B:
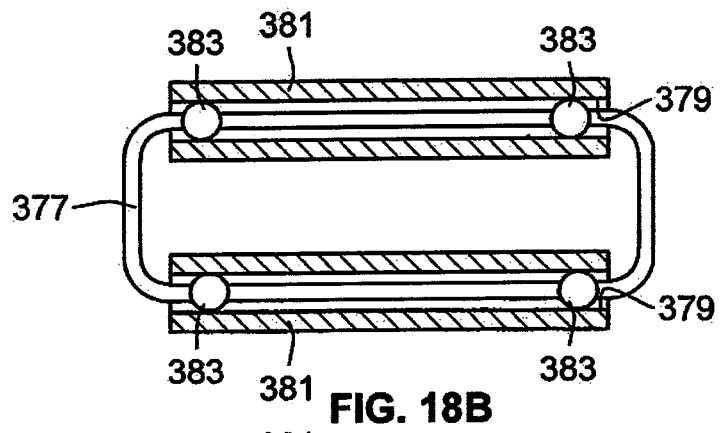
Figure 18C:
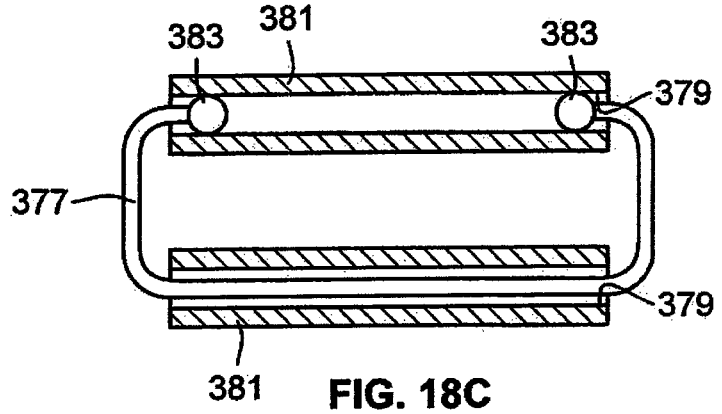
Figure 18D:
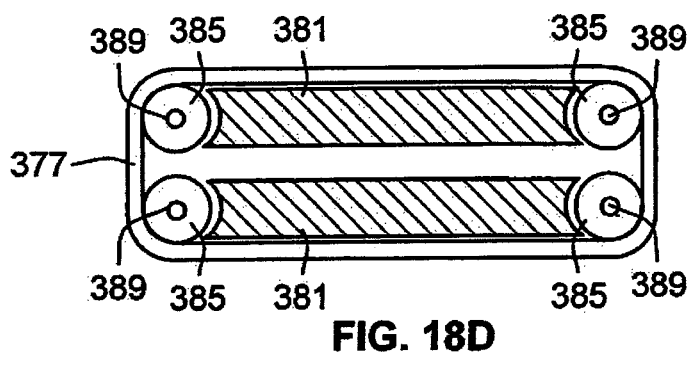

Turning to FIGS. 18A-D, there are seen four alternatives in which the resilient member comprises a single continuous member 337 per beam set and in which the resilient member 377 extends axially through an elongated passageway 379 in the beams 381 (e.g. see FIG. 14C). Alternatively, the beams 381 may have a U-shaped cross section that seats the elastic member 377. The continuous elastic member 377 may be unsecured to the members of the beam set, as shown in FIG. 18A. Alternatively, the resilient member may be affixed to one or more of the beams at one or more location, as shown in FIGS. 18B and 18C, in which the enlarged portion 383 of the elastic member represents a point of affixation. The manner of affixation is not critical, and may be any of a number of methods that would occur to a person skilled in the art, such as using an adhesive, welding, etc. In FIG. 18B the resilient member 377 is affixed in both ends of both beams 381. In FIG. 18C, the resilient member 377 is fixed at both ends of a single beam 381. Under such circumstances, the resilient member 377 does not necessarily need to be a continuous loop, and the portion interior of the beams 381 between the affixation points 383 is not required. In a further embodiment, the beam members 381 may be provided with friction reducing means for the resilient member, so as to provide for a more consistent application of closing force. For example, the ends of the beams 381 may be provided with rolling elements, such as the sleeves 385, mounted for rotation on pins 387, as shown in FIG. 18D. Also, as noted above, while the embodiments of FIG. 18A-D utilize a single resilient member 377, two or more such resilient members could be utilized to achieve the desired closure force.

Figure 19A:
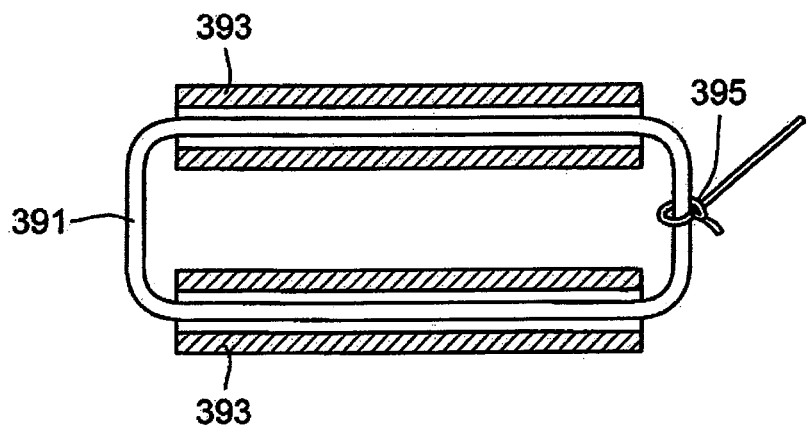
FIGS. 19A-E illustrates five embodiments of an occlusion apparatus utilizing a single closure element associated with both beams of the occlusion apparatus in which the closure element has substantially less elasticity than the resilient members of the previous examples.
Figure 19B:
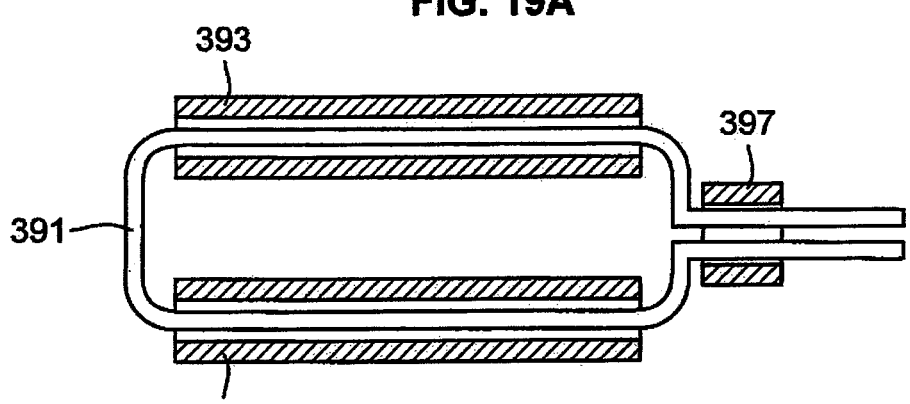

Further alternative configurations are shown in FIGS. 19A-E in which a single continuous closure element 391 is used. The closure element 391 is, in general, substantially less resilient or elastic than the resilient members described above, and may comprise, for example, an endo loop. As shown in FIG. 19A, the closure element 391 may be threaded through both beam members 393 and then tied off in a knot 395. The beam members 393 may be brought into proximity by pulling on the portion of the closure element 391 proximal to the knot 395. Further, resilient members such as those described above, may be applied to the ends of the beams 393 to maintain the closure force, or the knot 395 may be a slip knot which would cinch down to maintain the spacing of the beams. With reference to FIG. 19B, the closure element 391 can be first located or positioned around the tissue or anatomical structure to be clamped or occluded, with the elongated beams 393 then being threaded over the opposite ends of the closure element 391. In FIG. 19B a ferrule 397 is used instead of a knot to apply a cinching force to the closure element.

Figure 19C:
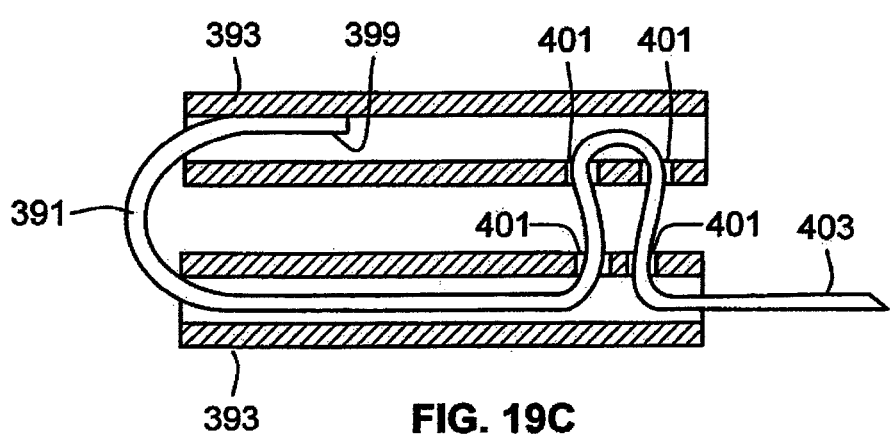
Figure 19D:
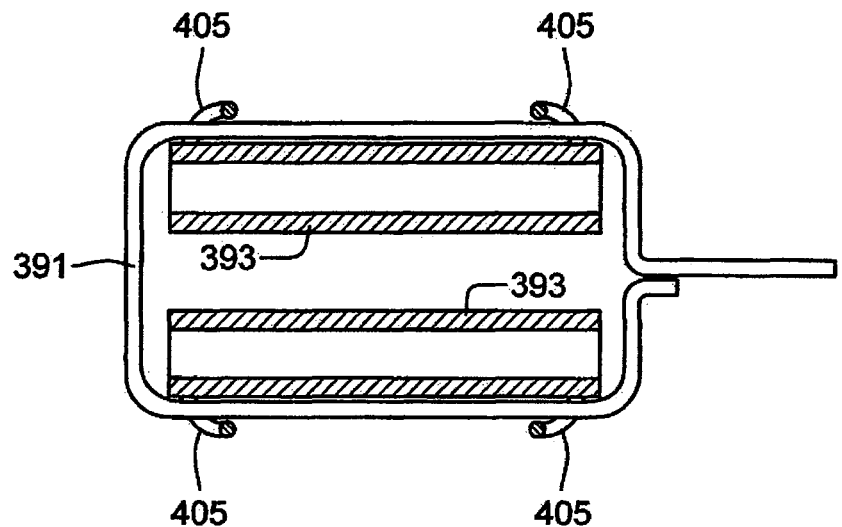
Figure 19E:
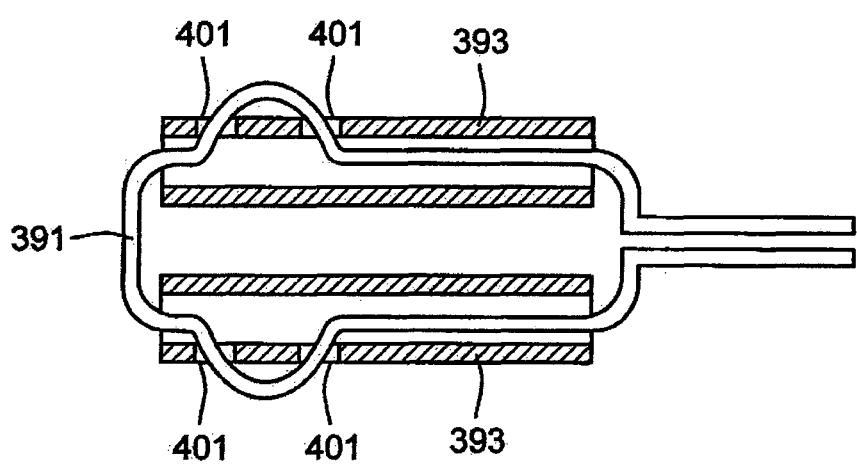

In FIG. 19C, one free end 399 of the closure element 391 is secured to one of the beams 393, and the closure element is threaded between the beam members through apertures 401 in beams such that it engages both beams. Closure force is applied to the beams 393 by pulling on the other free end 403 of the closure element 391, and the apertures 401 cooperate to act like a buckle to lock the closure element 391 relative to the beams. In FIG. 19D, the beams 393 are provided with external stirrups or eyelets 405 adjacent each end through which the closure element is threaded. In FIG. 19E, the beam members 393 are provided with a series of holes 451 which the closure element 391 is threaded through.

Having shown and described various examples of an embodiment according to the present disclosure, further adaptations of the methods, components and systems described herein may be accomplished by appropriate modifications by one of ordinary skill in the art without departing from the scope of the disclosure. Several of such potential modifications have been mentioned, and still others will be apparent to those skilled in the art. For instance, the examples, embodiments, geometries, materials, dimensions, steps, and the like discussed above are illustrative and are not necessarily required. Accordingly, the scope of the present disclosure should be considered in terms of the following claims and is understood not to be limited to the details of structure and operation shown and described in the specification and drawings.

As set forth above, the described device includes the aspects set forth below, with each of the aspects being susceptible of use with any of the other aspects, as is appropriate.

In accordance with one aspect, an apparatus is provided for occluding an anatomical structure comprising a first beam having first and second ends; a second beam having first and second ends; at least a first resilient/elastic member connecting the first beam member and the second beam member; and wherein the first resilient member applies a force to the first beam member and the second beam sufficient to occlude the anatomical structure.

In accordance with another aspect, an occlusion apparatus further comprises at least a second resilient member connecting the second end of the first beam member to the second end of the second beam member wherein the second resilient member is stretched to facilitate connection to the second end of the second beam member when the occlusion apparatus.

In accordance with another aspect, an occlusion apparatus is provided wherein the second resilient member is connected to the second end of the first beam member when the occlusion apparatus is in an open position, and wherein the second resilient member is stretched to facilitate connection to the second end of the second beam when the occlusion apparatus is in the closed position.

In accordance with another aspect, an occlusion apparatus is provided wherein the first and second beam members are substantially rigid.

In accordance with another aspect, an occlusion apparatus is provided wherein when the occlusion apparatus is in the closed position, the first and second resilient members generate a pressure applied by the first and second beam members within an operating range of 2-12 psi.

In accordance with another aspect, an occlusion apparatus is provided wherein the first and second resilient members have an equivalent effective resiliency.

In accordance with another aspect, an occlusion apparatus is provided wherein the first and second beam members are adapted to apply an even distribution of pressure along their lengths when in the closed position.

In accordance with another aspect, an occlusion apparatus is provided wherein the first resilient member is in the form of a loop or, alternatively, is discontinuous.

In accordance with another aspect, an occlusion apparatus is provided wherein the first resilient member is connected to the first beam member by a pin.

In accordance with another aspect, an occlusion apparatus is provided wherein the second resilient member is not connected to the second beam member when the occlusion apparatus is in the open position but is connected to the second beam member by a pin when the occlusion apparatus is in a closed position.

In accordance with another aspect, an occlusion apparatus is provided wherein the occlusion apparatus is configured to permit an anatomical structure to be passed between the first and second beam members when in the open position.

In accordance with another aspect, a system for occluding an anatomical structure is provided comprising an occlusion apparatus according to the aspects described above; a deployment device in which the deployment device is adapted to hold the occlusion apparatus in an open position for locating the occlusion apparatus adjacent an anatomical structure to be occluded; and the deployment device further comprises a primary mover adapted to move the occlusion apparatus to a closed position and a secondary mover adapted to lock the occlusion apparatus in the closed position.

In accordance with another aspect, a system is provided wherein the primary mover further comprises a cinching member.

In accordance with another aspect, a system is provided wherein the cinching member further comprises a suture.

In accordance with another aspect, a system is provided wherein the secondary mover is further adapted to release the occlusion apparatus from the deployment device.

In accordance with another aspect, a system is provided wherein the deployment device further comprises a shaft having a distal end; first and second jaws coupled to the distal end of the shaft and biased toward an open position; first and second shuttle bodies slidably connected to the respective first and second jaws; the first and second shuttle bodies being adapted to releasably connect the occlusion apparatus to the respective first and second jaws when the first and second shuttle bodies are in a first position relative to the first and second jaws; and wherein the jaws are movable to a closed position after which the shuttle bodies are movable to a second position relative to the first and second jaws wherein the occlusion apparatus is released from the deployment device.

In accordance with another aspect, a system is provided that comprises a cable coupled to the jaws and adapted to control the opening position of the first and second jaws.

In accordance with another aspect, a system is provided wherein the deployment device further comprises a resilient retainer coupled to the shuttle bodies and that tends to bias the jaws toward an open position.

In accordance with another aspect, a system is provided wherein the first and second jaws of the deployment device are pivotably connected to each other.

What is claimed is:

1. An occlusion apparatus deployment device comprising:
   an operator control handle;
   an elongated shaft operatively coupled to the operator control handle;
   a coupling head operatively coupled to the elongated shaft;
   a pair of jaws repositionably mounted to the coupling head, the jaws repositionable between a non-parallel open position and a parallel, closed position;
   an occlusion apparatus including a first beam and a second beam operatively coupled to one another;
   a cable operatively coupled to the operator control handle and operatively coupled to at least one of the pair of jaws, the cable configured to be tensioned to reposition at least one of the jaws between the parallel closed position and the non-parallel open position;
   wherein a first resilient member, separate from the first and second beams, is mounted to the first and second beams to bias the first and second beams toward one another, the first resilient member extending outbound of and longitudinally along both the first and second beams.

2. An occlusion apparatus deployment device comprising:
   an operator control handle;
   an elongated shaft operatively coupled to the operator control handle;
   a coupling head operatively coupled to the elongated shaft;
   a pair of jaws repositionably mounted to the coupling head, the jaws repositionable between a non-parallel open position and a parallel, closed position;
   an atraumatic occlusion device including a first beam repositionably mounted to a second beam by way of a spring, the first beam repositionable with respect to the second beam between a non-parallel position and a parallel position, wherein a first longitudinal end of the first beam includes a first seat configured to receive a first pin, wherein a second longitudinal end of the second beam includes a second seat configured to receive a second pin;

a cable operatively coupled to the operator control handle and operatively coupled to at least one of the pair of jaws, the cable configured to be tensioned to reposition at least one of the jaws between the closed position and the open position;

wherein the first pin is operatively coupled to a first of the jaws, and wherein the second pin is operatively coupled to a second of the jaws, the first of the jaws is operatively coupled to the first beam when the first pin is received within the first seat, and the second of the jaws is operatively coupled to the second beam when the second pin is received within the second seat.

3. An occlusion apparatus deployment device comprising: an operator control handle; an elongated shaft operatively coupled to the operator control handle: a pair of linear jaws repositionably mounted with respect to one another proximate a distal end of the shaft, the jaws repositionable between an open position and a closed position, each of the jaws including a longitudinal concavity configured to receive at least a portion of an occlusion apparatus therein, where the longitudinal concavities face one another; an occlusion device including a first beam repositionably mounted to a second beam by way of a spring separate from the first and second beams and extending between the first and second beams, the first beam repositionable with respect to the second beam between an open position and a closed position, at least one of the first beam and the second beam covered by a sock, wherein a first jaw of the pair of linear jaws is positioned on a first side of the occlusion device, and wherein a second jaw of the pair of linear jaws is positioned on a second side of the occlusion device, the first side faces opposite from the second side; wherein the pair of linear jaws is releasably coupled to the occlusion device; a cable operatively coupled to the operator control handle and operatively coupled to at least one of the pair of jaws, the cable configured to be tensioned to reposition at least one of the jaws between the closed position and the open position.

\* \* \* \* \*